(12) United States Patent
Pennock et al.

(10) Patent No.: US 10,794,525 B2
(45) Date of Patent: Oct. 6, 2020

(54) FLUID TRANSFER ASSEMBLY

(71) Applicant: SAINT-GOBAIN PERFORMANCE PLASTICS CORPORATION, Solon, OH (US)

(72) Inventors: Brandon J. Pennock, Midland, MI (US); Clemens E. Zoellner, Bay City, MI (US); Gerald M. Pennington, Wesley Chapel, FL (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 613 days.

(21) Appl. No.: 14/948,020

(22) Filed: Nov. 20, 2015

(65) Prior Publication Data

US 2016/0146392 A1  May 26, 2016

Related U.S. Application Data

(60) Provisional application No. 62/083,018, filed on Nov. 21, 2014.

(51) Int. Cl.
*F16L 47/20* (2006.01)
*F16L 31/00* (2006.01)
(Continued)

(52) U.S. Cl.
CPC ............ *F16L 47/20* (2013.01); *A61M 39/10* (2013.01); *F16L 47/06* (2013.01); *B29C 65/562* (2013.01); *B29C 66/1222* (2013.01); *B29C 66/1224* (2013.01); *B29C 66/1282* (2013.01); *B29C 66/1284* (2013.01); *B29C 66/1286* (2013.01); *B29C 66/12841* (2013.01); *B29C 66/12861* (2013.01); *B29C 66/30321* (2013.01);
(Continued)

(58) Field of Classification Search
CPC ........ F16L 31/00; F16L 47/20; F16L 2201/44
USPC .............................. 285/239, 242, 382, 382.7
See application file for complete search history.

(56) References Cited

U.S. PATENT DOCUMENTS 3,468,346 A * 9/1969 Smith ..................... B29C 65/00
138/109
3,540,223 A * 11/1970 Ebbe ....................... A01G 25/02
138/109
(Continued)

FOREIGN PATENT DOCUMENTS

CN 201078546 Y 6/2008
CN 101977653 A 2/2011
(Continued)

OTHER PUBLICATIONS

International Search Report for PCT/US2015/061971 dated Mar. 2, 2016, 1 page.
(Continued)

*Primary Examiner* — Anna M Momper
*Assistant Examiner* — Fannie C Kee
(74) *Attorney, Agent, or Firm* — Abel Schillinger, LLP; Chi Suk Kim

(57) ABSTRACT

A leak-proof fluid transfer assembly including a thermoplastic tube, a thermoset tube, and connector coupling the thermoplastic tube and the thermoset tube, where the fluid transfer assembly is adapted to maintain a substantially leak-proof fluid connection between the thermoplastic tube and the thermoset tube after autoclave sterilization.

20 Claims, 2 Drawing Sheets

(51) Int. Cl.
*A61M 39/10* (2006.01)
*F16L 47/06* (2006.01)
*B29C 65/00* (2006.01)
*B29C 65/56* (2006.01)

(52) U.S. Cl.
CPC .......... *B29C 66/5221* (2013.01); *B29C 66/71* (2013.01); *B29C 66/7392* (2013.01); *B29C 66/7394* (2013.01); *B29C 66/73941* (2013.01); *F16L 31/00* (2013.01); *F16L 2201/44* (2013.01)

(56) References Cited

U.S. PATENT DOCUMENTS

| | | | | |
|---|---|---|---|---|
| 3,975,039 | A | * | 8/1976 | Penneck ............... B29C 65/68 156/86 |
| 4,457,542 | A | * | 7/1984 | Shaefer ............... F16L 43/008 156/172 |
| 5,305,799 | A | * | 4/1994 | Dal Palu ............... F16L 11/11 138/109 |
| 5,364,130 | A | | 11/1994 | Thalmann |
| 7,922,213 | B2 | * | 4/2011 | Werth ............... F16L 33/2071 285/242 |
| 7,980,602 | B2 | | 7/2011 | Charlson et al. |
| 2005/0082826 | A1 | | 4/2005 | Werth |
| 2006/0170134 | A1 | | 8/2006 | Rowley et al. |
| 2009/0243284 | A1 | | 10/2009 | Klingel, Jr. et al. |
| 2010/0059985 | A1 | | 3/2010 | Nielson |
| 2010/0063477 | A1 | | 3/2010 | Ohigawa |
| 2011/0163533 | A1 | | 7/2011 | Snyder et al. |
| 2012/0223517 | A1 | | 9/2012 | Morrissey et al. |
| 2013/0043676 | A1 | | 2/2013 | Baker |
| 2013/0140811 | A1 | | 6/2013 | Fahrer et al. |
| 2014/0091569 | A1 | | 4/2014 | Spohn et al. |

FOREIGN PATENT DOCUMENTS

| | | |
|---|---|---|
| EP | 0769516 A2 | 4/1997 |
| EP | 2383503 A1 | 11/2011 |
| EP | 2314904 B1 | 3/2014 |
| WO | 0054960 A1 | 9/2000 |
| WO | 2011082221 A1 | 7/2011 |
| WO | 2012150991 A2 | 11/2012 |
| WO | 2016081893 A1 | 5/2016 |

OTHER PUBLICATIONS

Extended European Search Report for EP15860452, completed Jun. 1, 2018, 10 pages.

* cited by examiner

FLUID TRANSFER ASSEMBLY

CROSS-REFERENCE TO RELATED APPLICATION(S)

This application claims priority under 35 U.S.C. § 119(e) to U.S. Patent Application No. 62/083,018 entitled "FLUID TRANSFER ASSEMBLY," by Brandon J. Pennock, et al., filed Nov. 21, 2014, which is assigned to the current assignee hereof and incorporated herein by reference in its entirety.

FIELD OF THE DISCLOSURE

The present disclosure relates to fluid transfer assemblies, and more particularly to fluid transfer assemblies adapted for connecting a thermoplastic tube and a thermoset tube.

RELATED ART

In the manufacturing and processing of various products, it often is desired to transfer fluid into or out of a closed processing system by connecting tubes of different materials, such as connecting a thermoplastic tube with a thermoset tube, and do so in a substantially aseptic, hygienic, or sterile manner and without breaching the closed nature of the system. One way to form a fluid connection between a thermoplastic tube and a thermoset tube includes coupling the tubes with a connector. However, leakage can occur at the connection because the thermoplastic tube and the thermoset tube interact with the connector in different ways. The leakage can be exacerbated when the connection is subjected to the extreme conditions of autoclave sterilization. In view of the above, there exists a need for improved fluid transfer assemblies that can accommodate different tubing materials and maintain a leak-proof environment, an aseptic environment, and the like. In particular, there exists a need for a fluid transfer assembly designed to prevent leakage at the connection between a thermoplastic tube and a thermoset tube, even after autoclaving.

BRIEF DESCRIPTION OF THE DRAWINGS

Embodiments are illustrated by way of example and are not limited in the accompanying figures.

Figure 1:
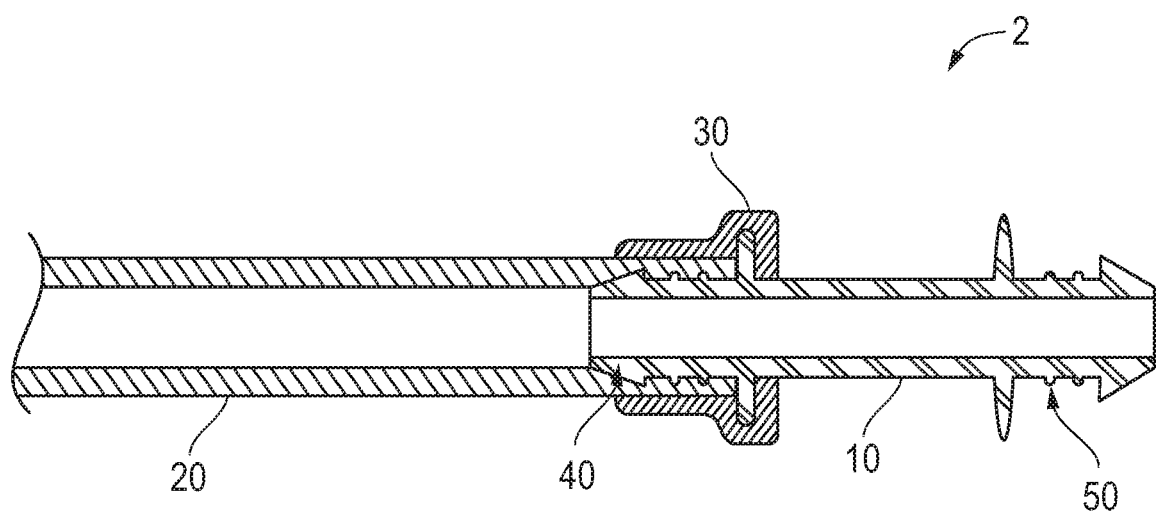
FIG. 1 includes an illustration of a cross-section of an embodiment of the fluid transfer assembly.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the fluid transfer arts.

The present disclosure is directed to improved fluid transfer assemblies demonstrating significant improvements over conventional fluid transfer assemblies. For example, certain embodiments can exhibit significant improvement in preventing leakage in a fluid connection between tubes comprising different materials, particularly a substantially leak-proof fluid connection between a thermoplastic tube and a thermoset tube. The term "substantially leak-proof" refers to a fluid connection that has a Submerged Leak Test or Autoclaved Submerged Leak Test rating of at least 75%, as described below, and can include a fluid connection having a rating of up to 100%, or a pass rating on a Side Load Leak Test, as described below. A particular advantage of certain embodiments of the fluid transfer assembly is the ability to provide a substantially leak-proof fluid connection between a thermoplastic tube and a thermoset tube even after autoclave sterilization. Another particular advantage of certain embodiments of the fluid transfer assembly is the ability to maintain an aseptic connection, as is understood in the art, between a thermoplastic tube and a thermoset tube, even after autoclave sterilization. These concepts are better understood in view of the embodiments described below that illustrate and do not limit the scope of the present invention.

In general, the fluid transfer assembly can include a connector coupled, or adapted to be coupled, with a thermoplastic tube and/or a thermoset tube. In certain embodiments, the fluid transfer assembly can include an additional coupling structure assisting in coupling the connector with the thermoplastic tube and/or a coupling structure assisting in coupling the connector with the thermoset tube.

FIG. 1 includes an illustration of a representative cross-section of an example fluid transfer assembly 2 according to certain embodiments. This exemplary fluid transfer assembly can include a connector 10, a thermoplastic tube 20, and a coupling structure 30.

Figure 2:
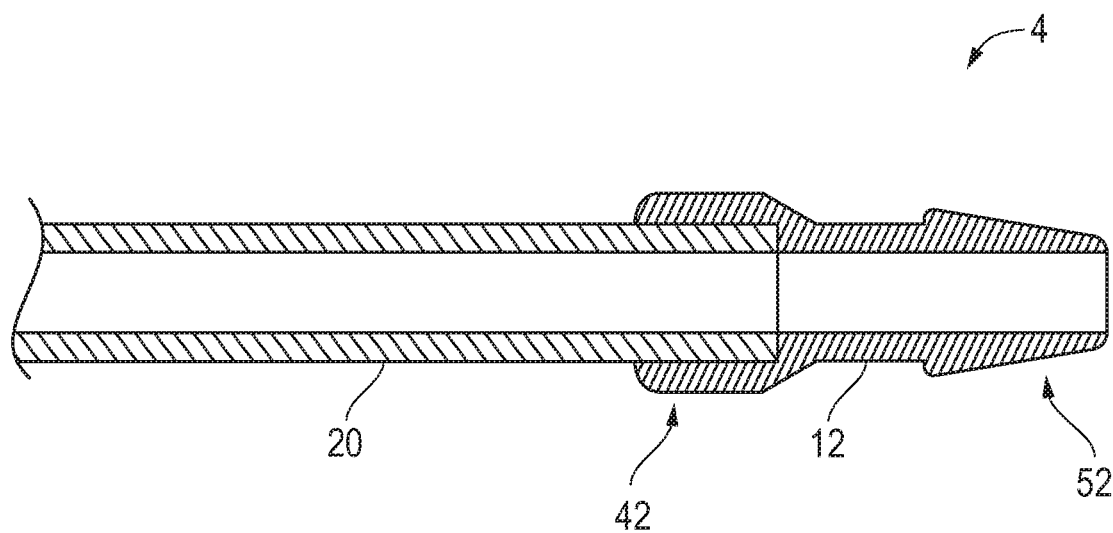
FIG. 2 includes an illustration of a cross-section of another embodiment of the fluid transfer assembly.

FIG. 2 includes an illustration of a representative cross-section of an example fluid transfer assembly 4 according to certain embodiments. This exemplary fluid transfer assembly can include a connector 12 and the thermoplastic tube 20, such as without the additional coupling structure.

It is to be understood that the fluid transfer assemblies illustrated in FIGS. 1 and 2 are illustrative embodiments. All of the items illustrated are not required, and any number of additional items, or fewer items, or different arrangement of items than shown is within the scope of the present disclosure.

As stated previously, the connector can be adapted to provide a fluid communication between a thermoplastic tube and a thermoset tube. To this end, the connector can include a thermoplastic tube attachment portion, a thermoset tube attachment portion, and a fluid connection between the thermoplastic tube attachment portion and the thermoset tube attachment portion.

In certain embodiments, the connector can include a non-reactive material, such as a material adapted for biopharmaceutical applications. In particular embodiments, the connector can comprise a material adapted to meet the critical demands of the medical, pharmaceutical, research, biotech and diagnostics industries. For example, the connector can comprise a material adapted for cell culture media and fermentation, diagnostic equipment, pharmaceutical, vaccine and botanical product production, pinch valves, high-purity water, reagent dispensing, medical fluid/drug delivery, dialysis and cardiac bypass, peristaltic pump segments, sterile filling and dispensing systems, and the like.

In certain embodiments, the connector can include a durable material that can withstand the extreme conditions of autoclave sterilization and maintain a seal with the thermoplastic tube and the thermoset tube. A particular aseptic environment may be desired for the above biopharmaceutical applications. In certain embodiments, the particular aseptic environment can be achieved by subjecting embodiments of the fluid transfer assembly to autoclave sterilization. Autoclave sterilization can include extreme conditions that can damage the connector. The damage to the connector can diminish the leak-proof properties of a fluid connection and contaminate the environment.

The thermoplastic polymer can include a variety of polymers suitable for the desired application. Traditionally, polyvinylidene difluoride (PVDF) has been used to withstand autoclave sterilization but could not readily form a sufficient seal with the thermoplastic tube. Other polymers that could readily form a sufficient seal suffered from deformation during autoclave sterilization and, thus, were not autoclavable. However, certain embodiments of the fluid transfer assembly described herein can include a connector comprising a seal-forming autoclavable material. A seal-forming autoclavable material refers to a material that can be subjected to autoclave sterilization without substantial deformation and readily form a sufficient seal, such as a leak-proof seal, with a thermoplastic tube. In particular embodiments, the seal-forming autoclavable material can include a thermoplastic polymer, such as a thermoplastic polymer produced without animal-derived components and/or phthalates. In more particular embodiments, the thermoplastic polymer can include a polypropylene. In even more particular embodiments, the polypropylene can include a P5M6k-080 brand polypropylene (available from Flint Hills Resources at Longview, Tex., USA)

Overall, it is a particular advantage of embodiments described herein that the connector can provide a seamless transition between the thermoplastic tube and the thermoset tube to maintain complete fluid integrity. In certain embodiments, the connector can have a smooth inner bore. In further embodiments, the connector has an inner diameter that corresponds to the inner diameters of the thermoplastic tube and the thermoset tube. When the diameter of the thermoplastic tube is greater than, or less than, the inner diameter of the thermoset tube, the connector can have a reducing inner diameter adapted to correspond to the different inner diameters and maintain fluid integrity. In very particular embodiments, the connector can include a PUREFIT® SIB® brand smooth inner bore (SIB) hose-barb connector (available from Saint-Gobain Performance Plastics Corporation at Beaverton, Mich., USA).

As discussed above, the connector can include a thermoplastic tube attachment portion and a thermoset tube attachment portion. The terms "thermoplastic tube attachment portion" and "thermoset tube attachment portion" refer to an attachment portion adapted for the thermoplastic or thermoset tube and do not necessarily indicate the composition of the particular attachment portion itself.

In addition, the connector can have a variety of configurations depending on the desired application, so long as there is an attachment portion for the thermoplastic tube and an attachment portion for the thermoset tube. For example, the connector can have attachment portions in an inline configuration, a cross configuration, a "Y" configuration, an elbow configuration, a "T" configuration, and the like. As discussed in more detail below, the attachment portions of the connector can be adapted to engage with their respective tubes in a variety of ways.

In certain embodiments, the thermoplastic tube attachment portion can be disposed on an inner diameter of the thermoplastic tube. Referring to FIG. 1, the connector can include a thermoplastic tube attachment portion 40 that includes a barb that grips the inner diameter of the tube. The barb can include one or more bumps or continuous ridges. For example, when the thermoplastic tube 20 is installed on the connector 10, the thermoplastic tube 20 can expand over the barb and form a seal as it relaxes to its original size beyond the barb.

In further embodiments, the thermoplastic tube attachment portion can be disposed on an outer diameter of the thermoplastic tube. Referring to FIG. 2, the thermoplastic tube attachment portion 42 can include an overmolded attachment portion where the thermoplastic attachment portion 42 is overmolded onto the outer diameter of the thermoplastic tube 20. In particular embodiments, the thermoplastic attachment portion 42 can be overmolded directly onto the outer diameter of the thermoplastic tube 20, free of any intervening layers. In very particular embodiments, the connector 12 can be an overmolded connector where the thermoplastic attachment portion 42 and the connector 12 is a monolithic piece.

As stated previously, the coupling of the thermoplastic tube with the thermoplastic tube attachment portion of the connector can be enhanced with the assistance of an additional coupling structure to maintain a substantially leak-proof connection and/or a substantially aseptic environment. The coupling structure can include a variety of types of coupling structure, such as a molded coupling structure, a mechanical coupling structure, and the like.

Referring again to FIG. 1, the coupling structure can include an overmolded coupling structure 30 in which the coupling structure is formed by overmolding. In certain embodiments, the polymeric material can be overmolded, such as directly overmolded free of any intervening layers, onto the outer diameter of the thermoplastic tube 20 and the outer surface of the connector 10. In certain embodiments, the overmolded coupling structure 30 can comprise a variety of polymers suitable for the desired application. In particular embodiments, the overmolded coupling structure can include the same or a different material than the material for the connector described above. In more particular embodiments, the overmolded coupling structure can include the same material as the connector.

In further embodiments, the coupling structure can include a mechanical coupling structure (not pictured), such as a fastener, including a clamp, a retainer system, a cable tie, a wrap tie, or a combination thereof. In particular embodiments, the mechanical coupling structure can include a multi-layer tubing retainer that provides a 360° compression force on the thermoplastic tube when assembled on the outer diameter of the thermoplastic tube. In very particular embodiments, the multi-layer tubing retainer can include a BARB LOCK® brand tubing retainer (available from Saint-Gobain Performance Plastics Corporation at Beaverton, Mich., USA).

In other embodiments, as illustrated in FIG. 2, a thermoplastic tube can be coupled with the thermoplastic tube attachment portion of the connector without an additional coupling structure and still maintain a substantially leak-proof connection and/or a substantially aseptic environment. For example, the thermoplastic tube attachment portion can include a thermoplastic tube attachment portion 42 disposed on an outer diameter of the thermoplastic tube 20. Although not illustrated, it is noted that the connection illustrated in FIG. 2 can include an additional coupling mechanism as described above.

As stated previously, the connector can also include a thermoset tube attachment portion adapted to be coupled with a thermoset tube, and, in certain embodiments, the fluid transfer assembly can include the thermoset tube coupled to the connector. The thermoset tube attachment portion can be adapted to be coupled with the thermoset tube in a variety of ways, as illustrated in FIGS. 3 and 4.

Figure 3:
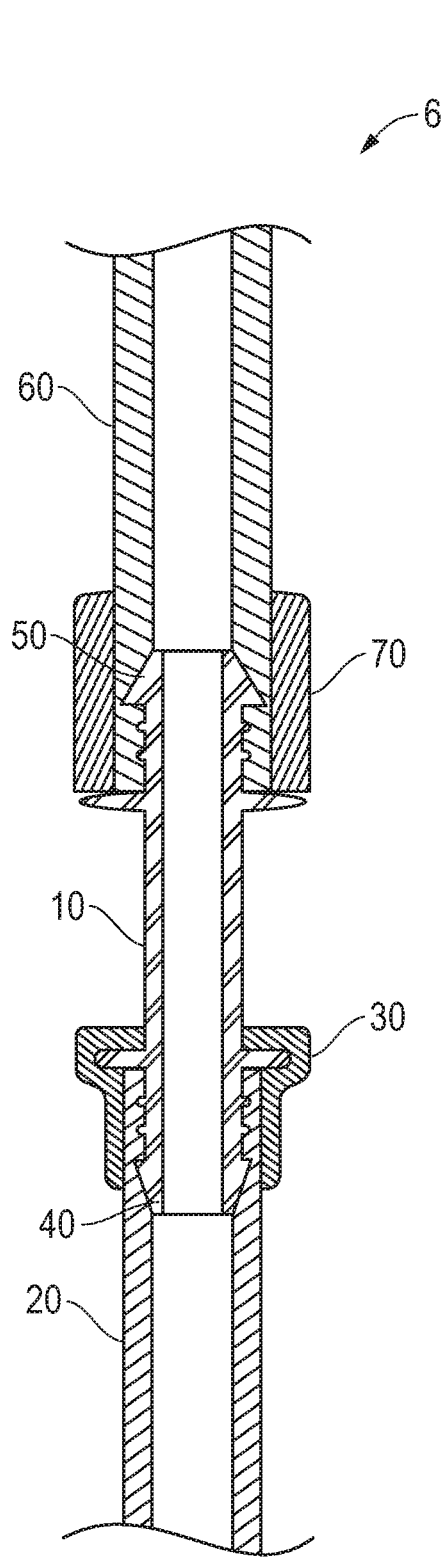
FIG. 3 includes an illustration of a cross-section of yet another embodiment of the fluid transfer assembly that includes a thermoset tube.

FIG. 3 includes an illustration of a representative cross-section of an example fluid transfer assembly 6 according to certain embodiments. This exemplary fluid transfer assembly can include the connector 10 and the thermoplastic tube 20 illustrated in FIG. 1, and can also include a thermoset tube 60 coupled to the connector 10 via the thermoset attachment portion 50 and, additionally, a coupling structure 70.

Figure 4:
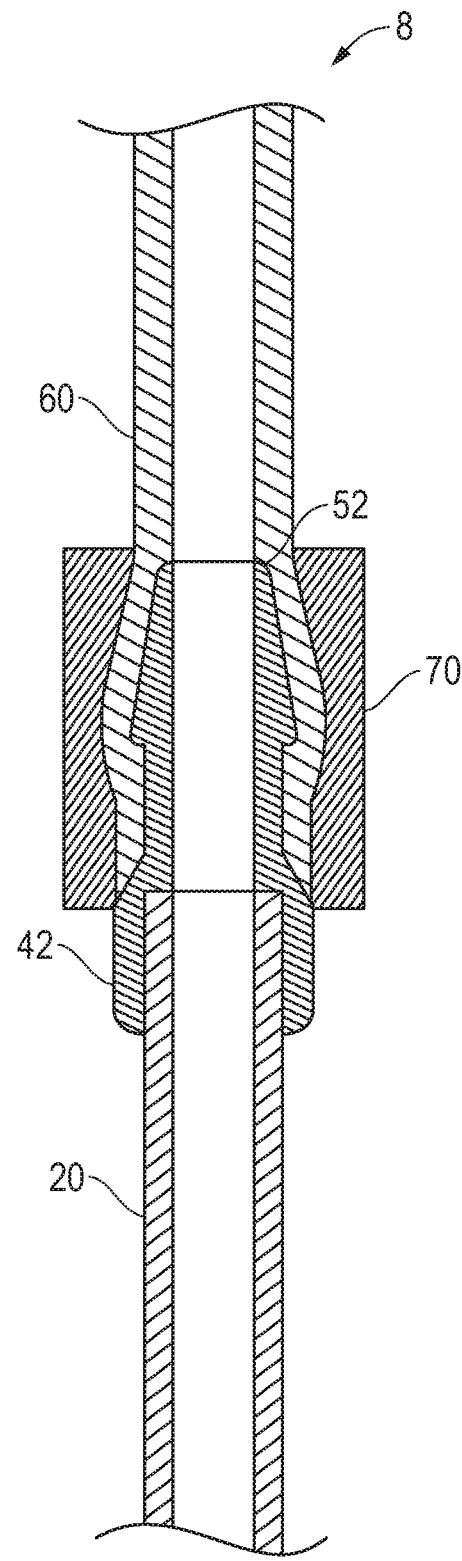
FIG. 4 includes an illustration of a cross-section of yet another embodiment of the fluid transfer assembly that includes a thermoset tube.

FIG. 4 includes an illustration of a representative cross-section of an example fluid transfer assembly 8 according to certain embodiments. This exemplary fluid transfer assembly can include the connector 12 and the thermoplastic tube 20 illustrated in FIG. 2, and also can include a thermoset tube 60 coupled to the connector 12 via the thermoset attachment portion 52 and, additionally, a coupling structure 70.

Is to be understood that the fluid transfer assemblies illustrated in FIGS. 3 and 4 are illustrative embodiments. All of the items illustrated are not required, and any number of additional items, or fewer items, or different arrangement of items than shown is within the scope of the present disclosure.

In certain embodiments, the thermoplastic tube attachment portion can be adapted to be disposed on an inner diameter of the thermoset tube. Referring to FIGS. 1 and 3, the connector 10 can include a thermoset tube attachment portion 50 that has the same shape, or substantially the same shape but different dimensions, as the thermoplastic tube attachment portion 40. In other particular embodiments, as illustrated in FIGS. 2 and 4, the connector can include a thermoset tube attachment portion 52 that has a substantially different shape than the thermoplastic attachment portion 42.

As illustrated in FIGS. 1-4, the thermoset tube attachment portion (50,52) can include a barb that is adapted to grip the inner diameter of the thermoset tube. As discussed above with respect to the thermoplastic attachment portion, the barb can include one or more bumps or continuous ridges as discussed above with respect to the attachment portion for the thermoplastic tube.

In certain embodiments, the thermoset tube can be mechanically coupled with the thermoset tube attachment portion. For example, as illustrated in FIG. 3, the thermoset tube can be installed on the connector 10 after the thermoset tube is formed. The attachment portion 50 can include a barb that grips the inner diameter of the thermoset tube 60, and the inner diameter of the thermoset tube 60 can expand over the barb and form a seal as it relaxes to its original size beyond the barb. In certain embodiments, the barb can include one or more bumps or continuous ridges.

In further embodiments, the thermoset tube can be molded onto the thermoset tube attachment portion. For example, as illustrated in FIG. 4, the thermoset tube 60 can be installed on the connector by overmolding the thermoset tube 60 onto the thermoset attachment portion 52. In particular embodiments, a thermoset tubing material can be overmolded onto the thermoset attachment portion 52 to form a thermoset tube coupled with the thermoset tube attachment portion. It should be understood that forming the thermoset tube on the connector is not limited to the example illustrated in FIG. 4. For example, the thermoset tube could be formed on a variety of connectors, such as the connector 10 illustrated in FIG. 3, depending on the application.

As with the thermoplastic tube, in certain embodiments, the coupling of the thermoset tube with the thermoset tube attachment portion of the connector can be enhanced with the assistance of an additional coupling structure to maintain a substantially leak-proof connection and a substantially aseptic environment. The coupling structure can include a variety of types of coupling structures, such as a molded coupling structure, a mechanical coupling structure, and the like.

The coupling structure can include an overmolded coupling structure (not illustrated) in which the coupling structure is formed by overmolding. In certain embodiments, the polymeric material can be overmolded, such as directly overmolded free of any intervening layers, onto the outer diameter of the thermoset tube 60 and the outer surface of the connector 10. In particular embodiments, the overmolded coupling structure can comprise a polymer, such as a thermoplastic polymer. In very particular embodiments, the thermoplastic polymer of the overmolded coupling structure can include a polypropylene.

In further embodiments, the coupling structure can include a mechanical coupling structure, such as a fastener, including a clamp, a retainer system, a cable tie, a wrap tie, or a combination thereof. In particular embodiments, the mechanical coupling structure can include a multi-layer tubing retainer that provides a 360° compression force on the thermoplastic tube when assembled on the outer diameter of the thermoplastic tube.

In certain embodiments, the mechanical coupling structure can be a polymeric coupling structure. In particular embodiments, the couplings structure can include a thermoplastic polymer. In very particular embodiments, the polymer can include a non-reactive thermoplastic polymer, such as a polyvinylidene difluoride (PVDF). In very particular embodiments, the multi-layer tubing retainer can include a PVDF BARBLOCK® brand tubing retainer (available from Saint-Gobain Performance Plastics Corporation at Beaverton, Mich., USA).

In certain embodiments, the fluid transfer assembly can include the thermoplastic tube. In particular embodiments, the thermoplastic tube can include a tube comprising a thermoplastic polymer, such as a thermoplastic elastomer. In very particular embodiments, the thermoplastic elastomer can include a styrene-based block copolymer, a thermoplastic olefin-based elastomer, a thermoplastic vulcanizate (TPV), a thermoplastic polyester-based elastomer, or any combination thereof.

In certain embodiments, the thermoplastic tube can include a biopharmaceutical thermoplastic tube. For example, the biopharmaceutical thermoplastic tube can be adapted to meet the critical demands of the medical, pharmaceutical, research, biotech and diagnostics industries. In particular embodiments, the biopharmaceutical thermoplastic tube can be adapted for cell culture media and fermentation, diagnostic equipment, pharmaceutical, vaccine and botanical product production, pinch valves, high-purity water, reagent dispensing, medical fluid/drug delivery, dialysis and cardiac bypass, peristaltic pump segments, sterile filling and dispensing systems, and the like. In very particular embodiments, the thermoplastic tube can include a C-FLEX® brand biopharmaceutical tubing (available from Saint-Gobain Performance Plastics Corporation at Clearwater, Fla., USA).

In certain embodiments, the thermoplastic tube can have an inner diameter of at least 0.4 cm, such as at least 0.6 cm, at least 0.8 cm, or even at least 1 cm. In further embodiments, the thermoplastic tube may have an inner diameter of no greater than 10 cm, such as no greater than 8 cm, or even no greater than 5 cm. For example, the thermoplastic tube can have an inner diameter in a range including one or more of the above minimums and maximums, such as in a range of 0.4 to 10 cm, 0.6 to 8 cm, or even 1 to 5 cm.

In certain embodiments, the thermoplastic tube can be treated to improve the adhesion to the connector. In particular embodiments, the treatment of the thermoplastic tube can include treatments such as mechanical or chemical etching, corona treating, c-treating, or any combination thereof.

As stated previously, the fluid transfer assembly can be adapted to be coupled to a thermoset tube or the thermoplastic tube can also include a thermoset tube. The thermoset tube can include a tube comprising a thermosetting polymer, such as a thermosetting elastomer. In certain embodiments, the thermosetting polymer can include a polyurethane elastomer, a silicone elastomer, or a combination thereof. In particular embodiments, the thermoset tube can include a silicone elastomer.

In certain embodiments, the thermoset tube can include a biopharmaceutical thermoset tube. For example, the biopharmaceutical thermoset tube can be adapted to meet the critical demands of the medical, pharmaceutical, research, biotech and diagnostics industries. In particular embodiments, the thermoset tube can be adapted for cell culture media and fermentation, diagnostic equipment, pharmaceutical, vaccine and botanical product production, pinch valves, high-purity water, reagent dispensing, medical fluid/drug delivery, dialysis and cardiac bypass, peristaltic pump segments, sterile filling and dispensing systems, and the like. In very particular embodiments, the thermoset tube can include a SANI-TECH® STHT®-C brand sanitary silicone tubing (available from Saint-Gobain Performance Plastics Corporation at Taunton, Mass., USA).

In certain embodiments, the thermoset tube can have an inner diameter of at least 0.4 cm, such as at least 0.6 cm, at least 0.8 cm, or even at least 1 cm. In further embodiments, the thermoset tube may have an inner diameter of no greater than 10 cm, such as no greater than 8 cm, or even no greater than 5 cm. For example, the thermoset tube can have an inner diameter in a range including one or more of the above minimums and maximums, such as in a range of 0.4 to 10 cm, 0.6 to 8 cm, or even 1 to 5 cm. In particular embodiments, the thermoset tube can have the same inner diameter as the thermoplastic tube. In other embodiments, the thermoset tube can have a greater or smaller inner diameter than the thermoplastic tube.

In certain embodiments, the thermoset tube can be treated to improve the adhesion to the connector. In particular embodiments, the treatment of the thermoplastic tube can include treatments such as mechanical or chemical etching, corona treating, c-treating, or any combination thereof.

The method of making the fluid transfer assembly can include providing a thermoplastic tube and coupling the thermoplastic tube with a connector. Coupling the thermoplastic tube with the connector can include overmolding the connector onto the thermoplastic tube or installing the thermoplastic tube on the attachment portion of the connector and then overmolding a coupling structure onto the thermoplastic tube and the attachment portion of the connector.

In certain embodiments, the method of making the fluid transfer assembly can further include adapting the connector to receive a thermoset tube, providing the thermoset tube, and coupling the thermoset tube to the attachment portion for the thermoset tube. As described above, the thermoset tube can be formed on the attachment portion or pre-formed and then installed on the attachment portion for the thermoset tube.

The connector, the thermoplastic tube, and the thermoset tube can each include any combination of the connectors and tubes described above.

In certain embodiments, the method of making the fluid transfer assembly can further include sterilizing the fluid transfer assembly. In certain embodiments, the sterilizing can include autoclave sterilization. In particular embodiments, the autoclave sterilization can include autoclaving the fluid transfer assembly with one or more autoclave cycles. In very particular embodiments, the autoclave sterilization can include at least one cycle, at least two cycles, or at least three cycles. The sterilizing treatment can be performed after coupling the thermoplastic tube with the thermoset tube.

In particular embodiments, each autoclave cycle can include a total cycle time of at least 0.5 hours, such as at least 0.7 hours, or even at least 0.9 hours. For example, each autoclaving cycle can include a total cycle time in a range of 0.5 to 3 hours, such as 0.7 to 2 hours, or even, 0.9 to 1.5 hours.

In particular embodiments, each autoclave cycle can include a maximum temperature of at least 100° C., such as at least 110° C., or even 120° C. For example, each autoclaving cycle can include a maximum temperature in a range of 100° C. to 200° C., such as at least 110° C. to 150° C., or even 120° C. to 130° C.

In particular embodiments, each autoclave cycle can include a maximum pressure of at least 14 psig, such as at least 16 psig, or even at least 18 psig. For example, each autoclaving cycle can include a maximum pressure in a range of 14 to 40 psig, such as 16 to 30 psig, or even 18 to 25 psig.

In certain embodiments, the fluid transfer assembly can maintain an aseptic connection, a substantially leak-proof connection, or both, between the thermoplastic tube and the thermoset tube, even after autoclave sterilization.

It is a particular advantage of certain embodiments of the fluid transfer assembly to maintain a substantially leak-proof connection between a thermoplastic tube and a thermoset tube. One way this particular advantage can be demonstrated is by subjecting embodiments of the fluid transfer assembly to a Submerged Leak Test. The purpose of the Submerged Leak Test is to determine whether the tested connection can be deemed as reliable, such as substantially leak-proof. The Submerged Leak Test can be performed on one side of the connection or on both sides of the connection, focused on whether there is leakage between the tube and the connector.

The Submerged Leak Test includes submerged pressure testing where a test technician watches for bubbles to form at the connection of interest indicating a leak. Care must be taken to ensure that the connection of interest of the tested samples are consistent, including depth of the hose on the connector, and that cuts in the tubes are square and clean.

The Submerged Leak Test includes attaching the trial fluid transfer assembly to a regulated high pressure air source at zero psig. The connection of interest is then manipulated to simulate natural handling and submerged in the water bath, ensuring good visibility. Once submerged, the digital gauge is activated and should indicate a pressure of 0 psig. The low pressure air inlet on the test cabinet is slowly opened to allow a test pressure to ramp up to a pressure of about 15 psi. The fluid transfer assembly is again manipulated to simulate a side load for about 1 second and then is observed for 10 minutes, until a failure is detected, or until the maximum safe pressure is reached. Failure in a submerged pressure test is defined as the point at which bubbles begin to issue from the connecting structure.

In certain embodiments, the fluid transfer assembly can have a Submerged Leak Test rating of at least 75%, at least 80%, at least 85%, at least 90%, or even at least 95%. The rating is related to the ratio of trials passing the test to total trial tested for given connector sample. In other words, the sample fluid transfer assembly includes a lot of trials that pass at the given percentage.

It is a particular advantage of certain embodiments of the fluid transfer assembly that the fluid transfer assembly can undergo autoclave sterilization and still achieve a substantially leak-proof fluid connection between a thermoplastic tube and a thermoset tube. It is understood that a seal formed between a tube and a connector can be disrupted by autoclave sterilization.

Without being limited to theory, one way in which the seal can be disrupted includes the contracting of the polymer material of the tube under the heat of autoclave sterilization. As another example, the polymer material of the tube can stretch, such as in a longitudinal direction, due to the elevated pressure during the autoclave sterilization. Despite the potential disruptions of the seal formed between the connector and the thermoplastic tube and between the connector and the thermoset tube, certain embodiments of the fluid transfer assembly can include an autoclaved fluid transfer assembly maintaining a substantially leak-proof connection between a thermoplastic tube and a thermoset tube.

This particular advantage can be illustrated by subjecting embodiments of the fluid transfer assembly to an Autoclaved Submerged Leak Test. The Autoclaved Submerged Leak Test is identical to the Submerged Leak Test, except that the Autoclaved Submerged Leak Test includes autoclave sterilizing the fluid transfer assembly prior to testing. In the autoclaved submerged leak test, the samples should be autoclave sterilized according to the following parameters:

Total cycles: 3
Total cycle time: 1 hour
Temperature: 124° C.+/−2° C.
Pressure: 21 psig+/−2 psi In certain embodiments, the fluid transfer assembly can have an Autoclaved Submerged Leak Test rating of at least 75%, at least 80%, at least 85%, at least 90%, or even at least 95%. As with the submerged leak test rating described earlier, the autoclaved rating is related to the ratio of trials passing the test to total trial tested for a given fluid transfer assembly sample. In other words, the sample fluid transfer assembly includes a lot of trials that pass at the given percentage.

It is a particular advantage of certain embodiments of the fluid transfer assembly that the fluid transfer assembly can undergo autoclave sterilization and achieve a substantially leak-proof fluid connection between a thermoplastic tube and a thermoset tube with a side load.

As discussed above, it is understood that a seal formed between a tube and a connector can be disrupted by autoclave sterilization. The leak-proof properties of a fluid connection can be further tested when subjected to a side load. For example, it is possible that a fluid connection could fail a Side Load Leak Test that would otherwise pass one of the submerged leak tests described above. However, the fluid connection according to certain embodiments described herein can also pass a Side Load Leak Test, as described below.

This particular advantage can be illustrated by subjecting embodiments of the fluid transfer assembly to an Autoclaved Submerged Leak Test wherein the connection of interest is manipulated to simulate natural handling and a side load on the connectors and submerged in the water bath, ensuring good visibility. Failure in a Side Load Leak Test is defined as the point at which bubbles begin to issue from the connecting structure with the side load.

In certain embodiments, the fluid transfer assembly can exhibit a Side Load Leak Test pass rating, meaning that no bubbles issue from the fluid connection with a side load under the condition described above.

In certain embodiments, the fluid transfer assembly can include a commercial lot of fluid transfer assemblies. In particular embodiments, a commercial lot of fluid transfer assemblies can include at least 5 fluid transfer assemblies, such as at least 10 fluid transfer assemblies, or even at least 15 fluid transfer assemblies. In further embodiments, a commercial lot of fluid transfer assemblies may include no greater than 30 fluid transfer assemblies, such as no greater than 25 fluid transfer assemblies, or even no greater than 20 fluid transfer assemblies.

In certain embodiments, the method described herein can include forming a commercial lot of fluid transfer assemblies including at least 5 fluid transfer assemblies, such as at least 10 fluid transfer assemblies, or even at least 15 fluid transfer assemblies. In further embodiments, the method described herein may include forming a commercial lot of fluid transfer assemblies including no greater than 30 fluid transfer assemblies, such as no greater than 25 fluid transfer assemblies, or even no greater than 20 fluid transfer assemblies. In particular embodiments, the commercial lots are sequential commercial lots. In other words, the commercial lots include sequentially manufactured fluid transfer assemblies.

In certain embodiments, the commercial lot can have a Submerged Leak Proof Test rating of at least 75%, at least 80%, at least 85%, at least 90%, or even at least 95%. In further embodiments, the commercial lot can have an Autoclaved Submerged Leak Test rating of at least 75%, at least 80%, at least 85%, at least 90%, or even at least 95%. In yet further embodiments, at least 50%, at least 755, or even 100% of the fluid transfer assemblies in the commercial lot can have a Side Load Leak Test rating of pass.

The concepts described herein will be further described in the following examples, which do not limit the scope of the invention described in the claims.

EXAMPLES

In the following Examples, a variety of fluid connections were subjected to one or more of the leak tests described above. The fluid connections represented a one or more sides of a fluid connection between a thermoplastic tube or a thermoset tube and a connector. The thermoplastic tube used was a C-FLEX® brand biopharmaceutical tubing (available from Saint-Gobain Performance Plastics Corporation at Clearwater, Fla., USA) and the thermoset tube used was a Sani-Tech STHT-C® brand sanitary silicone tubing (available from Saint-Gobain Performance Plastics Corporation at Taunton, Mass., USA). The thermoplastic tube and the thermoset tube each had a ½-inch inner diameter. Sample 1 tested the thermoset side of the fluid connection and Samples 2-6 tested the thermoplastic side of the fluid connection.

Sample 1 included 18 different trials of an embodiment of the fluid transfer assembly described above including a thermoset tube was secured to a ½-inch polypropylene (PPAF) PUREFIT® SIB® smooth inner bore (SIB) hose-barb connector (available from Saint-Gobain Performance Plastics Corporation at Beaverton, Mich., USA) using a polyvinylidene difluoride (PVDF) 500 series BAR-BLOCK® brand tubing retainer (available from Saint-Gobain Performance Plastics Corporation at Beaverton, Mich., USA).

Sample 2 included 18 different trials of an embodiment of the fluid transfer assembly described above including a thermoplastic tube and a thermoset tube secured to a ¼" PPAF SIB connector. The connection between the thermoplastic tube and the connector included a PPAF overmolded coupling mechanism. Further the connection between the thermoset tube and the connector included a PVDF 252 series BARBLOCK® brand tubing retainer (available from Saint-Gobain Performance Plastics Corporation at Beaverton, Mich., USA).

Sample 3 included a 18 different trials of a fluid connection including a thermoplastic tube secured to a ½-inch PVDF PUREFIT® SIB® brand hose-barb connector (available from Saint-Gobain Performance Plastics Corporation at Beaverton, Mich., USA) overmolded with polypropylene.

Sample 4 was identical to Sample 3 except that Sample 4 further included two O-rings disposed on the hose-barb connector.

Sample 5 was identical to Sample 4 except that Sample 5 included only one O-ring disposed on the hose-barb connector.

Sample 6 was identical to Sample 5 except that the Sample 6 connection was subjected to a conventional plasma treatment to open bond sites on the hose-barb connector to increase bonding of the materials.

Sample 7 was identical to Sample 3 except that the Sample 7 connection was subjected to a conventional plasma treatment to open bond sites on the hose-barb connector to increase bonding of the materials.

Sample 8 included 18 different trials of a fluid connection including the thermoset tube and PPAF connector used in Sample 1, and the tube was attached to the connector using an industry standard nylon zip tie.

A plurality of each of the samples were tested (up to 18 trials) according to the Autoclaved Submerged Leak Test described above and Samples 1, 2, and 7 were also subjected to the Side Load Leak Test described above. The Autoclaved Submerged Leak Test included 3 autoclave cycles of 121° C. for 20 minutes per cycle. If bubbles were observed, the sample was given a rating of FAIL. If no bubbles were observed, the sample was given a rating of PASS. The results of the Autoclaved Submerged Leak Test for each of Samples 1-7 are provided below in Table 1. The results of the Side Load Leak Test for each of Samples 1, 2, and 7 are provided below in Table 2.

TABLE 1

| Trial No. | Sample 1 | Sample 2 | Sample 3 | Sample 4 | Sample 5 | Sample 6 | Sample 7 | Sample 8 |
| --- | --- | --- | --- | --- | --- | --- | --- | --- |
| 1 | PASS | PASS | -FAIL- | -FAIL- | -FAIL- | -FAIL- | -FAIL- | PASS |
| 2 | PASS | PASS | PASS | -FAIL- | -FAIL- | -FAIL- | -FAIL- | -FAIL- |
| 3 | PASS | PASS | PASS | -FAIL- | -FAIL- | -FAIL- | -FAIL- | PASS |
| 4 | PASS | PASS | PASS | -FAIL- | -FAIL- | -FAIL- | -FAIL- | -FAIL- |
| 5 | PASS | PASS | -FAIL- | -FAIL- | -FAIL- | -FAIL- | -FAIL- | -FAIL- |
| 6 | PASS | PASS | PASS | -FAIL- | -FAIL- | -FAIL- | -FAIL- | PASS |
| 7 | PASS | PASS | -FAIL- | -FAIL- | -FAIL- | -FAIL- | -FAIL- | PASS |
| 8 | PASS | PASS | PASS | -FAIL- | -FAIL- | -FAIL- | -FAIL- | -FAIL- |
| 9 | PASS | PASS | -FAIL- | -FAIL- | -FAIL- | -FAIL- | -FAIL- | PASS |
| 10 | PASS | PASS | -FAIL- | -FAIL- | -FAIL- | -FAIL- | -FAIL- | PASS |
| 11 | PASS | PASS | PASS | n/a | n/a | n/a | n/a | -FAIL- |
| 12 | PASS | PASS | -FAIL- | n/a | n/a | n/a | n/a | PASS |
| 13 | PASS | PASS | -FAIL- | n/a | n/a | n/a | n/a | PASS |
| 14 | PASS | PASS | PASS | n/a | n/a | n/a | n/a | PASS |
| 15 | PASS | PASS | PASS | n/a | n/a | n/a | n/a | PASS |

TABLE 1-continued

| Trial No. | Sample 1 | Sample 2 | Sample 3 | Sample 4 | Sample 5 | Sample 6 | Sample 7 | Sample 8 |
|---|---|---|---|---|---|---|---|---|
| 16 | PASS | PASS | PASS | n/a | n/a | n/a | n/a | PASS |
| 17 | PASS | PASS | PASS | n/a | n/a | n/a | n/a | PASS |
| 18 | PASS | PASS | PASS | n/a | n/a | n/a | n/a | PASS |

As shown in Table 1, Samples 1 and 2 received a 100% PASS rating. Sample 3 failed 7 out of 18 trials for a 61% pass rating. Samples 4-7 each received a 0% pass rating and testing was terminated after 10 trials due to the rate of failure. For Sample 8, 5 of the 18 trials failed for a 72% pass rating. Thus, the results of the Autoclaved Submerged Leak Test illustrate the superior leak-proof properties of embodiments of the fluid transfer assemblies described herein.

TABLE 2

| Trial No. | Sample 1 | Sample 2 | Sample 7 |
|---|---|---|---|
| 1 | PASS | PASS | --FAIL-- |
| 2 | PASS | PASS | --FAIL-- |
| 3 | PASS | PASS | --FAIL-- |
| 4 | PASS | PASS | --FAIL-- |
| 5 | PASS | PASS | --FAIL-- |
| 6 | PASS | PASS | --FAIL-- |
| 7 | PASS | PASS | --FAIL-- |
| 8 | PASS | PASS | --FAIL-- |
| 9 | PASS | PASS | --FAIL-- |
| 10 | PASS | PASS | --FAIL-- |
| 11 | PASS | PASS | --FAIL-- |
| 12 | PASS | PASS | --FAIL-- |
| 13 | PASS | PASS | --FAIL-- |
| 14 | PASS | PASS | --FAIL-- |
| 15 | PASS | PASS | --FAIL-- |
| 16 | PASS | PASS | --FAIL-- |
| 17 | PASS | PASS | --FAIL-- |
| 18 | PASS | PASS | --FAIL-- |

As shown in Table 2, each trial of Samples 1 and 2 has a rating of pass on the Side Load Leak Test, whereas not one of the trials for Sample 7 was able to pass the Side Load Leak Test. Thus, the results of the Side Load Leak Test also illustrate the superior leak-proof properties of embodiments of the fluid transfer assemblies described herein.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. A leak-proof fluid transfer assembly comprising:
a thermoplastic tube;
a thermoset tube;
a connector coupling the thermoplastic tube and the thermoset tube,
wherein the fluid transfer assembly is adapted to maintain a substantially leak-proof fluid connection between the thermoplastic tube and the thermoset tube after autoclave sterilization.

Item 2. A method of forming a leak-proof fluid transfer assembly comprising:
providing a thermoplastic tube;
coupling the thermoplastic tube with a connector;
coupling a thermoset tube with the connector,
wherein the fluid transfer assembly is adapted to maintain a substantially leak-proof fluid connection between the thermoplastic tube and the thermoset tube after autoclave sterilization.

Item 3. The method or fluid transfer assembly of any one of the preceding items, wherein the fluid transfer assembly has a Submerged Leak Test rating of at least 75%, at least 80%, at least 85%, at least 90%, or even at least 95%.

Item 4. The method or fluid transfer assembly of any one of the preceding items, wherein the fluid transfer assembly has an Autoclaved Submerged Leak Test rating of at least 75%, at least 80%, at least 85%, at least 90%, or even at least 95%.

Item 5. The method or fluid transfer assembly of any one of the preceding items, wherein the fluid transfer assembly has a Side Load Leak Test rating of pass.

Item 6. The method of any one of items 2-5, wherein the coupling of the thermoplastic with the connector includes overmolding.

Item 7. The method of any one of items 2-6, wherein coupling the thermoplastic tube with the connector includes overmolding a coupling structure on the thermoplastic tube and the connector.

Item 8. The method of item 7, wherein the coupling structure includes a polymer.

Item 9. The method of item 8, wherein the polymer includes a thermoplastic polymer.

Item 10. The method of item 9, wherein the thermoplastic polymer includes a polypropylene.

Item 11. The method of any one of items 2-10, wherein coupling the thermoplastic tube with the connector includes overmolding the connector on the thermoplastic tube.

Item 12. The method of item 11, wherein overmolding the connector on the thermoplastic tube includes providing a polymer material and overmolding the polymer material on the thermoplastic tube to form the connector.

Item 13. The method of any one of items 11 or 12, wherein overmolding the connector on the thermoplastic tube includes overmolding the polymer material directly on the thermoplastic tube free of any intervening layers.

Item 14. The method of any one of items 12 or 13, wherein the polymer material includes a thermoplastic polymer.

Item 15. The method of item 14, wherein the thermoplastic polymer includes a polypropylene.

Item 16. The method of any one of items 2-15, wherein coupling the thermoplastic tube with the connector includes treating the thermoplastic tube to improve the adhesion to the connector.

Item 17. The method of item 16, wherein treating the thermoplastic tube includes mechanical etching, chemical etching, corona treating, c-treating, or any combination thereof.

Item 18. The method of any one of items 2-17, wherein coupling the thermoplastic tube with the connector includes providing an additional coupling mechanism on the thermoplastic tube and the connector.

Item 19. The method of item 18, wherein the additional coupling mechanism includes a mechanical coupling structure.

Item 20. The method of item 19, wherein the mechanical coupling structure includes a clamp, a retainer system, a cable tie, a wrap tie, or a combination thereof.

Item 21. The method of item 20, wherein the retainer system includes a multi-layer tubing retainer that provides a 360° compression force on the thermoplastic tube when assembled on the outer diameter of the thermoplastic tube.

Item 22. The method of any one of items 2-21, wherein coupling the thermoset tube with the connector includes providing a thermoset tube and mechanically installing the thermoset tube on the connector.

Item 23. The method of any one of items 2-22, wherein coupling the thermoset tube with the connector includes forming the thermoset tube onto the connector.

Item 24. The method of item 23, wherein forming the thermoset tube onto the connector includes providing a polymer material and forming the polymer material into a thermoset tube on the connector.

Item 25. The method of item 24, wherein the polymer material is a thermosetting polymer material.

Item 26. The method of item 25, wherein the thermosetting polymer includes a polyurethane elastomer, a silicone elastomer, or a combination thereof.

Item 27. The method of item 26, wherein the thermosetting polymer includes a silicone elastomer.

Item 28. The method of any one of items 2-27, wherein coupling the thermoset tube with the connector includes treating the thermoset tube to improve the adhesion to the connector.

Item 29. The method of item 28, wherein treating the thermoset tube includes mechanical etching, chemical etching, corona treating, c-treating, or any combination thereof.

Item 30. The method of any one of items 2-29, wherein coupling the thermoplastic tube with the connector includes providing an additional coupling mechanism on the thermoplastic tube and the connector.

Item 31. The method of item 30, wherein the additional coupling mechanism includes a mechanical coupling structure.

Item 32. The method of item 31, wherein the mechanical coupling structure includes a clamp, a retainer system, a cable tie, a wrap tie, or a combination thereof.

Item 33. The method of item 32, wherein the retainer system includes a multi-layer tubing retainer that provides a 360° compression force on the thermoplastic tube when assembled on the outer diameter of the thermoplastic tube.

Item 34. The method of any one of items 2-33, further comprising subjecting the fluid transfer assembly to sterilization.

Item 35. The method of item 34, wherein the sterilization includes autoclave sterilization.

Item 36. The method of item 35, wherein the autoclave sterilization includes a plurality of autoclave cycles.

Item 37. The method of item 35, wherein the autoclave sterilization includes a plurality of autoclave cycles each having a total cycle time of at least 0.5 hours, at least 0.7 hours, or at least 0.9 hours.

Item 38. The method of any one of items 35-37, wherein the autoclave sterilization includes a plurality of autoclave cycles each having a maximum temperature of at least 100° C., at least 110° C., or at least 120° C.

Item 39. The method of any one of items 35-38, wherein the autoclave sterilization includes a plurality of autoclave cycles each having a maximum pressure of at least 14 psig, at least 16 psig, or at least 18 psig.

Item 40. The method or fluid transfer assembly of any one of the preceding items, wherein the thermoplastic tube includes a tube comprising a thermoplastic elastomer.

Item 41. The method or fluid transfer assembly of any one of the preceding items, wherein the thermoplastic tube includes a thermoplastic elastomer comprising a styrene-based block copolymer, a thermoplastic olefin-based elastomer, a thermoplastic vulcanizate (TPV), a thermoplastic polyester-based elastomer, or any combination thereof.

Item 42. The method or fluid transfer assembly of any one of the preceding items, wherein the thermoplastic tube includes a biopharmaceutical thermoplastic tube.

Item 43. The method or fluid transfer assembly of any one of the preceding items, wherein the thermoplastic tube has an inner diameter of at least 0.4 cm, at least 0.6 cm, at least 0.8 cm, or at least 1 cm.

Item 44. The method or fluid transfer assembly of any one of the preceding items, wherein the thermoplastic tube has an inner diameter of no greater than 10 cm, no greater than 8 cm, or no greater than 5 cm.

Item 45. The method or fluid transfer assembly of any one of the preceding items, wherein the thermoplastic tube has an inner diameter in a range of 0.4 to 10 cm, 0.6 to 8 cm, or 1 to 5 cm.

Item 46. The method or fluid transfer assembly of any one of the preceding items, wherein the connector is adapted to provide a fluid communication between the thermoplastic tube and the thermoset tube.

Item 47. The method or fluid transfer assembly of any one of the preceding items, wherein the connector has an inner diameter that is substantially the same as the inner diameter of the thermoplastic tube, of the thermoset tube, or of both.

Item 48. The method or fluid transfer assembly of any one of the preceding items, wherein the connector has a reducing inner diameter adapted to connect tubes having different inner diameters.

Item 49. The method or fluid transfer assembly of any one of the preceding items, wherein the connector can has a smooth inner bore.

Item 50. The method or fluid transfer assembly of any one of the preceding items, wherein the connector includes a material adapted for biopharmaceutical applications.

Item 51. The method or fluid transfer assembly of any one of the preceding items, wherein the connector includes a polymeric connector.

Item 52. The method or fluid transfer assembly of any one of the preceding items, wherein the connector comprises a thermoplastic polymer.

Item 53. The method or fluid transfer assembly of any one of the preceding items, wherein the connector comprises a polypropylene.

Item 54. The method or fluid transfer assembly of any one of the preceding items, wherein the connector has an inline configuration, a cross configuration, a "Y" configuration, an elbow configuration, or a "T" configuration.

Item 55. The method or fluid transfer assembly of any one of the preceding items, wherein the connector includes an attachment portion disposed on an outer diameter of the thermoplastic tube.

Item 56. The method or fluid transfer assembly of any one of the preceding items, wherein the connector includes an attachment portion that includes a barb adapted to grip an inner diameter of the thermoplastic tube.

Item 57. The method or fluid transfer assembly of any one of the preceding items, wherein the connector includes an attachment portion that includes a barb adapted to grip an inner diameter of the thermoset tube.

Item 58. The method or fluid transfer assembly of any one of items 56 and 57, wherein the barb includes one or more bumps or continuous ridges.

Item 59. The method or fluid transfer assembly of any one of the preceding items, wherein the connector comprises an overmolded connector.

Item 60. The method or fluid transfer assembly of any one of the preceding items, wherein the thermoset tube includes a tube comprising a thermosetting elastomer.

Item 61. The method or fluid transfer assembly of any one of the preceding items, wherein the thermoset tube includes a tube comprising a polyurethane elastomer, a silicone elastomer, or a combination thereof.

Item 62. The method or fluid transfer assembly of any one of the preceding items, wherein the thermoset tube includes a tube comprising a silicone elastomer.

Item 63. The method or fluid transfer assembly of any one of the preceding items, wherein the thermoset tube includes a biopharmaceutical thermoset tube.

Item 64. The method or fluid transfer assembly of any one of the preceding items, wherein the thermoset tube has an inner diameter of at least 0.4 cm, at least 0.6 cm, at least 0.8 cm, or at least 1 cm.

Item 65. The method or fluid transfer assembly of any one of the preceding items, wherein the thermoset tube has an inner diameter of no greater than 10 cm, no greater than 8 cm, or no greater than 5 cm.

Item 66. The method or fluid transfer assembly of any one of the preceding items, wherein the thermoset tube has an inner diameter in a range of 0.4 to 10 cm, 0.6 to 8 cm, or 1 to 5 cm.

Item 67. The method or fluid transfer assembly of any one of the preceding items, wherein the thermoset tube has an inner diameter that is the same as an inner diameter of the thermoplastic tube.

Item 68. The method or fluid transfer assembly of any one of the preceding items, wherein the thermoset tube has an inner diameter that is greater than an inner diameter of the thermoplastic tube.

Item 69. The method or fluid transfer assembly of any one of the preceding items, wherein the thermoset tube has an inner diameter that is less than an inner diameter of the thermoplastic tube.

Item 70. The method or fluid transfer assembly of any one of the preceding items, wherein the thermoset tube is bonded to the connector.

Item 71. The method or fluid transfer assembly of any one of the preceding items, wherein the fluid transfer assembly is an autoclaved fluid transfer assembly.

Item 72. The method or fluid transfer assembly of any one of the preceding items, wherein the fluid transfer assembly is adapted to maintain an aseptic connection between the thermoplastic tube and the thermoset tube.

Item 73. The method or fluid transfer assembly of any one of the preceding items, wherein the fluid transfer assembly is adapted to maintain an aseptic connection between the thermoplastic tube and the thermoset tube after autoclaving.

Item 74. The method or fluid transfer assembly of any one of the preceding items, wherein the fluid transfer assembly is adapted to maintain a substantially leak-proof fluid connection between the thermoplastic tube and the thermoset tube.

Item 75. The method or fluid transfer assembly of any one of the preceding items, wherein the fluid transfer assembly is adapted to maintain a substantially leak-proof fluid connection between the thermoplastic tube and the thermoset tube after autoclaving.

Item 76. A commercial lot of fluid transfer assemblies, wherein the commercial lot includes at least 5 fluid transfer assemblies and has an Autoclaved Submerged Leak Proof Test rating of at least 75%.

Item 77. A method of forming a commercial lot of fluid transfer assemblies, wherein the commercial lot includes at least 5 fluid transfer assemblies and has an Autoclaved Submerged Leak Proof Test rating of at least 75%.

Item 78. The commercial lot or method of items 76 or 77, wherein the commercial lot has an Autoclaved Submerged Leak Test rating of at least 75%, at least 80%, at least 85%, at least 90%, or even at least 95%.

Item 79. The commercial lot or method of items 76-78, wherein the commercial lot or method includes the leak-proof fluid transfer assembly or method of any one of items 1-75.

Item 80. The commercial lot or method of any one of items 76-79, wherein the commercial lot includes at least 10 leak-proof fluid transfer assemblies.

Item 81. The commercial lot or method of any one of items 76-80, wherein the commercial lot includes at least 15 leak-proof fluid transfer assemblies.

Item 82. The commercial lot or method of any one of items 76-81, wherein the commercial lot includes no greater than 20 leak-proof fluid transfer assemblies.

Item 83. The commercial lot or method of any one of items 76-82, wherein at least 50%, such as at least 75%, or even 100% of the fluid transfer assemblies has a Side Load Leak Test rating of pass.

Item 84. The commercial lot or method of any one of items 76-83, wherein the commercial lot is a sequential commercial lot.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A leak-proof fluid transfer assembly comprising:
a thermoplastic tube;
a thermoset tube;
a connector coupling the thermoplastic tube and the thermoset tube, wherein the connector comprises a plurality of barbs adapted to grip an inner diameter of the thermoplastic tube,
wherein the fluid transfer assembly is adapted to maintain a substantially leak-proof fluid connection between the thermoplastic tube and the thermoset tube after autoclave sterilization, wherein at least one of the plurality of barbs includes one or more bumps, and wherein the connector comprises a first coupling structure on an outer diameter of the thermoplastic tube and a second coupling structure on an outer diameter of the thermoset tube, wherein at least one of the first coupling structure of the second coupling structure comprises polyvinylidene difluoride (PFDF).

2. The fluid transfer assembly of claim 1, wherein the thermoplastic tube includes a thermoplastic elastomer comprising a styrene-based block copolymer, a thermoplastic olefin-based elastomer, a thermoplastic vulcanizate (TPV), a thermoplastic polyester-based elastomer, or any combination thereof.

3. The fluid transfer assembly of claim 1, wherein the connector is adapted to provide a fluid communication between the thermoplastic tube and the thermoset tube.

4. The fluid transfer assembly of claim 1, wherein the connector includes a material adapted for biopharmaceutical applications.

5. The fluid transfer assembly of claim 1, wherein the connector comprises a polypropylene.

6. The fluid transfer assembly of claim 1, wherein the thermoset tube includes a tube comprising a polyurethane elastomer, a silicone elastomer, or a combination thereof.

7. The fluid transfer assembly of claim 1, wherein the thermoset tube includes a tube comprising a silicone elastomer.

8. The fluid transfer assembly of claim 1, wherein the fluid transfer assembly is adapted to maintain an aseptic connection between the thermoplastic tube and the thermoset tube after autoclaving.

9. The fluid transfer assembly of claim 1, wherein the fluid transfer assembly has a Submerged Leak Test rating of at least 75%.

10. The fluid transfer assembly of claim 1, wherein the fluid transfer assembly has an Autoclaved Submerged Leak Test rating of at least 75%.

11. The fluid transfer assembly of claim 1, wherein the thermoplastic tube has an inner diameter of at least 0.4 cm.

12. The fluid transfer assembly of claim 1, wherein the thermoplastic tube has an inner diameter of no greater than 10 cm.

13. The fluid transfer assembly of claim 1, wherein the connector has an inner diameter that is substantially the same as the inner diameter of the thermoplastic tube, of the thermoset tube, or of both.

14. The fluid transfer assembly of claim 1, wherein at least one of the other of the first coupling structure or the second coupling structure comprises polypropylene.

15. The fluid transfer assembly of claim 1, wherein the connector comprises a thermoplastic polymer.

16. The fluid transfer assembly of claim 1, wherein the connector has an inline configuration.

17. The fluid transfer assembly of claim 1, wherein at least one of the plurality of barbs includes one or more continuous ridges.

18. The fluid transfer assembly of claim 1, wherein the thermoset tube includes a tube comprising a polyurethane elastomer.

19. The fluid transfer assembly of claim 1, wherein the connector comprises an external rib that abuts an end of the thermoplastic tube.

20. The fluid transfer assembly of claim 19, wherein the first coupling structure overmolds the external rib of the connector.

* * * * *